United States Patent [19]

Khanna et al.

[11] Patent Number: 4,518,701

[45] Date of Patent: May 21, 1985

[54] REDUCTION IN NON-SPECIFIC INTERFERENCE IN HYDROPHOBIC LIGAND ASSAYS

[75] Inventors: Pyare L. Khanna, San Jose; Floyd W. Colvin, Redwood City, both of Calif.

[73] Assignee: Syntex (U.S.A.) Inc., Palo Alto, Calif.

[21] Appl. No.: 500,503

[22] Filed: Jun. 2, 1983

[51] Int. Cl.³ ............................................. G01N 33/52
[52] U.S. Cl. .................................... 436/500; 436/529; 436/800; 436/825
[58] Field of Search ................. 436/500, 529, 800, 825

[56] References Cited

PUBLICATIONS

Smith et al., Chem. Abstracts, 89, (1978), #74057.
Lisi et al., Clinica Chimica Acta, 120, (1982), pp. 171–179.

Primary Examiner—Christine M. Nucker
Attorney, Agent, or Firm—Bertram I. Rowland; Theodore J. Leigereg

[57] ABSTRACT

Methods are provided for reducing non-specific interference in competitive protein binding assays employing as the labeled reagent a fluorescent conjugate of a hydrophobic ligand conjugated to a fluorescer, which in turn is bound to a water soluble polysaccharide carrier ("fluorescer conjugate reagent"). In order to reduce non-specific interference from physiologic samples, the fluorescent reagent is combined with a lipid substituted neutral support, under conditions which provides two binding fractions: a first weakly binding fraction which is relatively free of non-specific interference in a competitive protein binding assay employing physiological fluids; and a second fraction, which more strongly binds to the lipid substituted support.

8 Claims, No Drawings

REDUCTION IN NON-SPECIFIC INTERFERENCE IN HYDROPHOBIC LIGAND ASSAYS

BACKGROUND OF THE INVENTION

1. Field of the Invention

A wide variety of techniques for determining low molecular weight ligands employing conjugates of low molecular weight ligands to fluorescers. In a somewhat more limited number of techniques, the ligand-fluorescer conjugate is joined to a polysaccharide carrier. Many of the ligands and fluorescers are highly hydrophobic. For example, polyiodothyronines conjugated to a fluorescer, such as fluorescein or fluorescein derivatives, can bind non-specifically to a wide variety of proteins which may be encountered in blood or other physiological sample. The problem is alleviated somewhat when the conjugate is bound to a polysaccharide carrier.

Where a polyiodothyronine is conjugated to a fluorescer, the presence of the heavy iodine atom may result in substantial quenching of the fluorescer. Non-specific binding of a protein to the polyiodothyronine may result in a change in the fluorescence. Due to patient sample variation, the degree to which the observed fluorescence changes at constant analyte concentration will vary with the source of the serum. Therefore, it is necessary to find some means to minimize the non-specific effect of the serum proteins on the observed results.

2. Description of the Prior Art

Co-pending application Ser. No. 411,180, filed Aug. 25, 1982, a continuation application of Ser. No. 17,874, teaches the use of a polysaccharide carrier with a polyiodothyronine-fluorescer conjugate to reduce non-specific interference with the fluorescence of the polyiodothyronine-fluorescer conjugate.

U.S. Pat. No. 3,988,943 describes a competitive protein binding assay employing ligand fluorescer conjugates, where the binding of antiligand inhibits the binding of antifluorescer. U.S. Pat. No. 3,996,345 describes an immunoassay employing a chromophore pair, where the chromophores are related by one of the chromophores quenching the fluorescence of the other one of the chromophores, where the amount of quencher brought within quenching distance of the fluorescing chromophore is related to the amount of analyte in the sample. Robbins, "Thyroxine-binding Proteins", Trace Components of Plasma: Isolation and Clinical Significance, Alan, R. Liss, Inc., New York, page 331 (1976) postulated that the inability of prealbumin to bind thyroxine-agarose affinity gels was related to the inability of the thyroxine to orient properly in the protein binding site.

SUMMARY OF THE INVENTION

Non-specific interference in competitive protein binding assays involving fluorescent labels and hydrophobic ligands is reduced. In assays involving a reagent having a fluorescer bound to a hydrophobic ligand, particularly a heavy atom containing ligand, where the ligand-fluorescer conjugate is further bound to a polysaccharide carrier ("fluorescer conjugate reagent") to reduce non-specific binding from components in a clinical sample, the non-specific binding is further reduced by contacting the fluorescer conjugate with lipid bound to a support (lipid reagent). The fluorescer conjugate is then separated from the lipid reagent, providing fluorescer conjugate reagent, which is substantially free of non-specific interference from materials in physiological fluids.

Compositions and kits are provided for use in the subject assays.

DESCRIPTION OF THE SPECIFIC EMBODIMENTS

Methods and compositions are provided for determining the presence in a physiological sample of a hydrophobic ligand or a receptor for such ligand, where a fluorescent label is employed, which is conjugated to the hydrophobic ligand. Where the ligand-fluorescer conjugate is then covalently bonded to a polysaccharide support to reduce non-specific interference from constituents of physiological fluids, the non-specific interference is further reduced by treating the ligand-fluorescer conjugate bound to the polysaccharide support ("fluorescer-conjugate reagent") with lipid bound to a support ("lipid reagent"). The fluorescer-conjugate reagent is separated into two binding fractions based on the degree of binding to the lipid reagent, the more weakly binding fraction serving as the fluorescer-conjugate reagent in a competitive protein binding assay for the hydrophobic ligand or receptor for the hydrophobic ligand.

The fluorescer-conjugate reagent which find use in the subject invention has three components: hydrophobic ligand; fluorescer; and macromolecular polysaccharide. A wide variety of hydrophobic ligands may be involved, such as steroids, lipids, terpenes, opiates, heavy atom containing compounds, e.g. polyiodothyronines having from 2 to 4 iodo groups, and polycyclic heterocyclic drugs. Of particular interest are the polyiodothyronines, more particularly, triiodothyronine and thyroxine. A wide variety of fluorescers may be employed, particularly xanthydrols, more particularly phenyl-substituted xanthydrols, such as fluorescein and substituted fluoresceins.

The supports will be polysaccharides such as dextran, amylose, etc., which may be modified by cross-linking, degradation, functionalization, or the like. Molecular weights will be at least about 35,000, and will normally be less than about 1 million, usually ranging from about 50,000 to about 500,000.

For the most part, the fluorescer conjugate reagents of the subject invention will have the following formula:

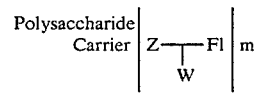

wherein:

The carriers have been described previously and may be any one of a variety of polysaccharides which are modified natural products or synthetic materials, which are water soluble, particularly dextran, starch and the like, naturally occurring or modified by cross-linking, functionalization, degradation or the like and more particularly functionalized with a linking group having from about 1 to 6 carbon atoms and usually providing an imino, amino or non-oxo carbonyl;

Z is a hydrophobic ligand, particularly a polyiodothyronine;

Fl is a fluorescer, particularly fluorescein or a fluorescein derivative;

W is a linking group bound to the carrier which is covalently bonded to an atom of the ligand-fluorescer conjugate Z-Fl;

m is preferably 1 and usually not exceeding 1 per 25 saccharide units.

Of particular interest in the subject invention are fluorescer conjugate reagents having the following formula:

wherein:

Carrier* is a dextran of from about 30,000 to 200,000 molecular weight, more usually of from about 35,000 to 100,000 molecular weight;

$Z^1$ is a tri- or tetraiodo-p-phenoxyphenol;

$Fl^1$ is a fluorescer, particularly fluorescein or fluorescein derivative, having an absorption maximum of at least 350 nm, preferably at least about 400 nm and more preferably 450 nm;

$m^1$ is 1 to 2.

In order to substantially eliminate non-specific interference resulting from constituents in physiological fluids, particularly serum, the subject compounds are treated under mild conditions with the lipid reagent, where the lipid reagent support is preferably a polysaccharide support. The same types of polysaccharides may be employed as described for the fluorescer conjugate reagent, but will generally be of substantially higher molecular weight, generally of at least about 200,000 molecular weight and will usually be selected so as to be insoluble in an aqueous medium, for example, agarose, sephadex, crosslinked dextran, cellulose, etc.

Prior to treatment with the lipid reagent, unreacted fluorescer contaminating the fluorescer-conjugate reagent may be removed by any convenient means. Sephadex chromatography has been found to be satisfactory.

The treatment of the fluorescer-conjugate reagent will normally involve contacting the fluorescer conjugate reagent with lipid reagent (lipid bound to a support) under conditions whereby one can separate weakly binding fluorescer conjugate reagent from strongly binding fluorescer conjugate reagent. Where a chromatographic technique is involved, the fluorescer conjugate reagent may give a fraction which moves through the void volume not retained by the column, and is the first material to move across the chromatogram. Additionally, there is a fraction which is weakly retained and a more strongly retained fraction. The weakly retained fraction is the material employed in the assay to be described. Conveniently, chromatographic columns will be employed with the lipid reagent having a polysaccharide support.

The lipid will generally be an aliphatic hydrocarbon of at least about 8, preferably at least about 10 carbon atoms and not more than 22 carbon atoms, usually not more than about 18 carbon atoms. The ratio of hydrocarbon molecules to molecular weight of the lipid bound support will generally be from about 1 to 40 weight percent, commercially available lipid modified supports, e.g. decylagarose, being satisfactory. See U.S. Pat. No. 3,917,527 for a description of lipid substituted supports. As a support, agarose is particularly desirable. Preferably, the aliphatic hydrocarbon will be a straight chain alkyl group of from about 10 to 14 carbon atoms, more preferably from about 10 to 12 carbon atoms.

About 1 ml of the lipid reagent will be used for about from $10^{-3}$ to $10^{-5}$ moles of the fluorescer conjugate reagent, where the fluorescer-conjugate reagent will generally be at a concentration of from about $10^{-2}$ to $10^{-5}$, more usually from about $10^{-2}$ to $10^{-4}$M. In preparing the column, normally, the column will be degassed by slowly stirring a suspension of the support under a mild vacuum, generally not less than about 10 mm Hg, and conveniently at room temperature. The chromatography of the fluorescer conjugate reagent will generally be under mild conditions, generally from about 15° to 40° C., more conveniently at ambient temperatures of from about 20° to 30° C.

Desirably, before chromatographing the fluorescer-conjugate reagent, the fluorescer-conjugate reagent and lipid reagent may be combined in an aqueous medium with mild agitation at ambient temperatures. About 1 ml of lipid reagent gel is combined with $10^{-2}$ to $10^{-5}$ moles of the fluorescer-conjugate reagent at a concentration in the range of about $10^{-2}$ to $10^{-6}$M. The mixture is agitated for at least about 5 min and less than about 6 h. The mixture may then be centrifuged and the resulting pellet suspended in an appropriate buffer and the suspension used for chromatography.

Prior to chromatographing the fluorescer-conjugate reagent, it is desirable to have a washing treatment. The washing treatment involves washing the fluorescer-conjugate reagent at the top of the column and the lipid reagent gel in the column with buffer in which there is no non-ionic detergent, so that the desired conjugate is not chromatographed and remains on the column. The amount of buffer which is employed is not critical, and is conveniently calculated in accordance with the formula in the experimental section. Two-fold differences in the calculated amounts are permissible.

In chromatographing the fluorescer conjugate reagent, which may have been treated previously, the fluorescer conjugate reagent is placed at the top of the lipid support column, which has normally been washed with a buffer. Any mild convenient buffer may be used, particularly phosphate, borate, carbonate or the like, generally at a pH in the range of about 7 to 9, preferably about 8. The buffer concentration will be relatively low, generally ranging from about 0.01 to 0.1M.

The fluorescer-conjugate reagent is eluted with a dilute solution of a non-ionic detergent, particularly a polyalkyleneoxy detergent, where the alkylene groups are of from about 2 to 3 carbon atoms. Of particular interest are non-ionic detergents which are alkyleneoxy modified polyolesters, particularly monoesters e.g. lauryl sorbitan, generally having a fatty acid group as a capping group at one end of from about 12 to 18, usually 12 to 16 carbon atoms. Particularly useful is Tween 20 at a concentration of from about 0.1 to 1% by weight, preferably of from about 0.4 to 0.6 weight percent, more preferably about 0.5%. The column may be eluted fairly rapidly, varying with the size and sample. A column of 1 ml of gel may be eluted at a rate of at least about 10 drops per minute, but generally not more than about 60 drops per minute, preferably not more than about 50 drops per minute. The fluid discharge from the column can be monitored by any convenient means, e.g. light absorption.

The resulting fluorescer conjugate reagent may now be used in fluorescent assays involving serum. Various fluorescent assays may be employed, such as those described in U.S. Pat. Nos. 3,996,345 and 4,318,707.

One assay may be used as examplary, which assay is referred to as triiodothyronine (T3) uptake, which is part of a thyroid function profile. In effect, by adding a predetermined amount of triiodothyronine to a serum sample, where the triiodothyronine is in excess of the available serum binding capacity for thyroxine, the binding sites of the serum proteins will be substantially saturated. There will be residual triiodothyronine which is then determined by providing for a competition between the residual triiodothyronine and the triiodothyronine-fluorescer conjugate bonded to the polysaccharide carrier for quencher labelled antibodies for triiodothyronine. The binding of the antibodies to the triiodothyronine conjugate results in quenching of fluorescence, which quenching is related to the amount of residual triiodothyronine. Optionally, one may add antifluorescer to quench any of the conjugate which is not bound to antiligand. In addition, a quenching chromophore may be conjugated to the antifluorescer to ensure substantially complete quenching of any fluorescer bound to antifluorescer.

In carrying out the assay for T3 uptake, an aqueous buffered medium is provided which includes the serum sample, ligand (a polyiodothyronine) at least equal to the binding capacity of the serum, antiligand to which a quencher molecule is conjugated (see U.S. Pat. No. 3,996,345), and the fluorescer conjugate reagent. While various orders of addition of the reagents may be employed, preferably the ligand and serum are combined in an aqueous medium, followed by antiligand followed by the fluorescer-conjugate reagent. Desirably, the first two stages will have incubations to allow for substantial equilibration of the system.

In assays for other than T3 uptake where a direct measure of a ligand or receptor is involved, the sample suspected of containing the analyte and, for ligand analyte, the reciprocal member of the specific binding pair (antiligand may be conjugated with quencher molecules), are combined with the fluorescer conjugate reagent, optionally followed by the addition of antifluorescer. One or more incubation steps may be involved.

Various dilutions and incubations may be employed in the assay. That is, before or concomitantly with each addition, additional aqueous medium may be added to provide for accurate transfer of reagents, increase of the volume as required by the measuring instrument, or the like. Incubation steps will normally vary from about 0.5 min to 6 h, usually from 1 min to 1 h, preferably from about 5 min to 0.5 h, more preferably from about 10 min to 0.5 h.

The aqueous assay medium may have up to 40% of an organic polar solvent, usually an oxy solvent i.e. hydroxylic or ethereal, such as ethanol, diethyl carbitol, tetrahydrofuran, glycerol, etc.

The aqueous medium will normally be buffered in the range of about 5 to 10, more usually in the range of about 6 to 9.5, and preferably in the range of about 7 to 9.5. Various buffers may be used, although one buffer may be preferred over another buffer in a particular situation. Illustrative buffers include borate, phosphate, barbital, tris, etc.

The temperatures during the various states of additions and measurements will generally be in the range of about 10° to 50° C., more usually in the range of about 15° to 45° C., and preferably in the range of about 15° to 40° C.

As indicated previously, the order of addition will vary widely, depending upon the particular materials employed, the manner of measurement, rate or equilibrium, and the like. However, the fluorescer-conjugate reagent will normally not be added to antiligand in the absence of the analyte.

In order to provide enhanced sensitivity and accuracy, the materials employed in the assay may be provided as kits. That is, the materials are prepared in predetermined ratios to enhance the response with variation in concentration over the range of interest.

The subject kits will have the fluorescer-conjugate reagent and antiligand to which quencher molecules are conjugated. Antifluorescer may be employed in place of or in addition to the quencher. The antibodies will normally be lyophilized and may be present by themselves or in combination with an appropriate amount of buffer, stabilizers or the like. The amount of buffer will be related to the dilution of the antibody to provide the aqueous reagent at the appropriate concentration. Normally, the antibodies will be in separate containers.

In the T3 uptake assay, the ratio of antibodies to the ligand as part of the fluorescent conjugate reagent will generally be in the range of about 0.25 to 1 mole per mole, more usually in the range of 0.5 to 1 mole per mole. The amount of antifluorescer when present in relation to the amount of fluorescer present as fluorescer-conjugate reagent will generally be present in from about 0.5 to 5 mole per mole, more usually about 0.75 to 3 mole per mole.

The following examples are offered by way of illustration and not by way of limitation:

EXPERIMENTAL

All temperatures not otherwise indicated are in centigrade. All percents and parts not otherwise indicated are by weight, except when two liquids are combined and the percents are by volume.

The following structural formulas are provided with numerical designations employed in the experimental examples.

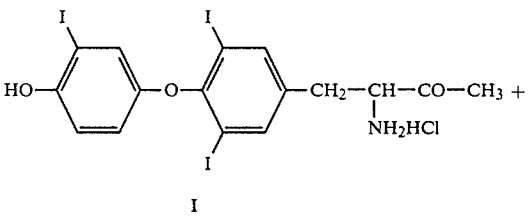

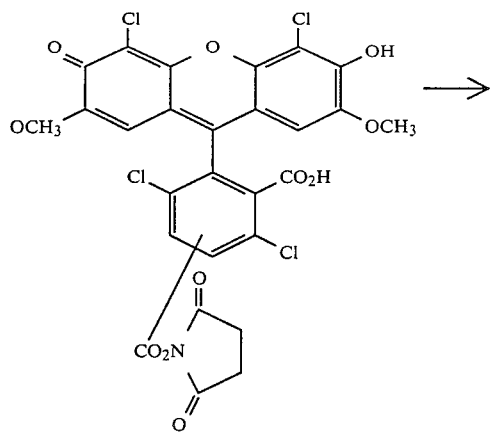
II (F540 NHS ester)
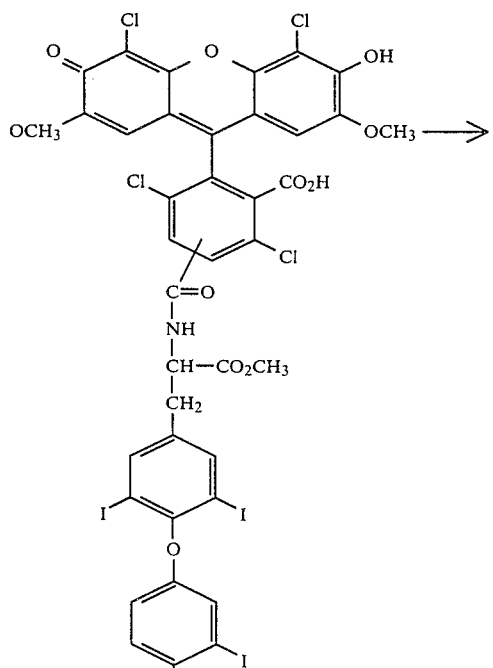
III
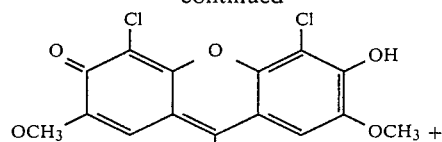
IVA
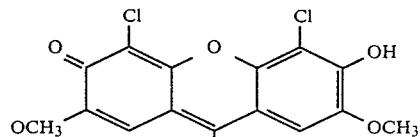
IVB
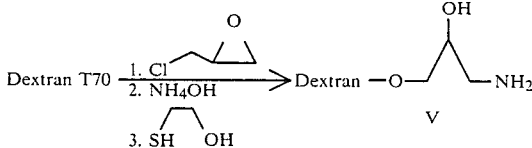
IVA + V ⟶ F540—T3—Dextran conjugate

EXAMPLE 1

Preparation of $F_{540}$-$T_3$ methyl ester (III) and the corresponding acid (IVA +B)

The solution of methyl triiodothyroninate hydrochloride (I), (500 mg), N-hydroxy succinimide ester of 9-(3',6'dichloro-2',4' or 5'-dicarboxyphenyl)-2,7-dimethoxy-4,5-dichloro-6-hydroxy-3-isoxanthenone ($F_{540}$) (II), from (500 mg $F_{540}$ using carbodiimide and N-hydroxy succinimide), triethylamine (500 μl), in dry dimethylformamide (DMF) was stirred overnight at room temperature. The DMF was removed on a rotovap at room temperature using a high vacuum pump. The residue was dissolved in cold 10% $Na_2CO_3$ (6 ml). The stirring cold (ice bath) solution was quickly acidified to pH 1.0 with conc. HCl. The orange precipitate was filtered and washed wit cold 10% HCl (8 ml). The precipitate was dried at room temperature under 0.01 mm Hg vacuum. TLC (Silica; 3:15:82; HOAc-Hexane-EtOAc) showed two major spots Rf 0.7 and 0.6 above the starting dye at Rf 0.3 and 0.2.

The material was purified by a reverse phase column (60.0 g RP-2 E. Merck, ca. 2×60 cm). The wet column was prepared in $CH_2Cl_2$. A tetrahydrofuran (THF) solution (25 ml) of the material was absorbed onto regular silica (ca 1.0 g), THF removed at room temperature on the rotovap and the absorbed silica placed on the reverse phase column. The column was eluted with 0.1% HOAc in $CH_2Cl_2$. Fractions (ca. 15 ml each) were taken and followed by TLC (same system as above). The product (III) was isolated as a mixture of the two major spots. (ca 340 mg). These were the first fluorescent material off the column.

III was dissolved in 1N NaOH (6 ml) and stirred at room temperature for one hour. The stirring solution was cooled in ice and acidified with conc. HCl to pH 1.0. The orange precipitate was filtered on a Buchner funnel and dried at room temperature at 0.01 mm Hg vacuum. TLC (Silica; 4:10:86, HOAc-Hexane-EtOAc) showed two major spots Rf. 0.6 and 0.45, plus two minor spots corresponding to the free dye.

The solid was purified by preparative TLC using 16 plates (Silica, 20 cm×20 cm, using the above TLC system). The two major bands were removed separately with MeOH. The MeOH was removed at room temperature on rotovap. Each residue was dissolved in a minimum of 10% $Na_2CO_3$, the solution filtered through a glass wool plug in a pipet, cooled in ice, acidified with conc. HCl. The precipitate was dried at room temperature over $P_2O_5$ at 0.002 mm Hg vacuum. 20 mg IVA (Rf. 0.45) acid and 140 mg IVB (Rf 0.6) was isolated.

The UV spectra in 0.05M $PO_4^{-3}$ pH 8.2 for Isomer IVA had $\lambda_{max}^{abs}$ 540 and Isomer IVB had $\lambda_{max}^{abs}$ 537. Their emission spectra excited at 500 nm were $\lambda_{max}^{emis}$ 553-54 (IVA) and $\lambda_{max}^{emis}$ 554-55 (IVB).

EXAMPLE 2

Preparation of Amino-Dextran (V)

Dextran (20.0 g; mol. wt 70,000) was dissolved in 25% aqueous $Zn(BF_4)_2$ (30 ml) and water (30 ml). The slurry was heated to 80° C. and epichlorohydrin (17 ml) added all at once with vigorous stirring. After 3 h of heating, the heat was turned off and stirring continued overnight (16 h). The dextran was precipitated by adding dropwise into stirring methanol (2 L). The precipitate was washed with acetone (500 ml) and dissolved in water (200 ml). To the dextran solution (220 ml) was added concentrated 14M $NH_4OH$ (100 ml) and the solution stirred overnight. The solution was again precipitated as before into MeOH (2 L), filtered, dried in vacuo and redissolved in 0.1M $NaHCO_3$—$Na_2CO_3$ buffer pH 9.0 (300 ml). β-Mercaptoethanol (3 ml) was added and the solution stirred overnight. The solution was dialyzed against $H_2O$, and lyophilized to give 14.0 g 3-amino-2hydroxypropyl ether of dextran. The number of amino groups was determined using 2,4,6-trinitrobenzenesulfonic acid (TNBS). Various lots were prepared with the number of amino groups varying from 3 to 25. The above procedure gave amino groups of 10 to 12 when repeated, the preferred range.

EXAMPLE 3

Preparation of $F_{540}$-$T_3$-Dextran Conjugate (VI)

A solution of IVA (3.0 mg), dicyclohexylcarbodiimide (2.7 mg), NHS (1.5 mg) in dry DMF was stirred at room temperature under nitrogen in the dark overnight (24 h). TLC (Silica, 1-49-50, HOAc:THF:$CH_2Cl_2$) indicated the absence of starting IVA, Rf 0.2).

The NHS ester solution was added dropwise to a cold (0°-5° C.) stirring solution of amino-dextran V (187 mg) in 0.05M phosphate, pH 8.0, buffer (6.2 ml). The pH of the solution was maintained with 5% $NaHCO_3$ at 8.1 to 8.3. After the addition was complete (ca. 30 min), the solution was stirred in the cold (0°-5° C.) in the dark overnight (20 h). A solution of 3N $NH_2OH$ (1.8 ml, pH 8.0) was added and stirring continued in the cold and dark for 2 h. The conjugate solution was then passed through a Sephadex G-50 column (100 ml) using phosphate buffer to remove unreacted fluorescer. The fast moving conjugate band was collected giving 23 ml conjugate solution with an O.D. at 545 nm of 1.67. This solution can be stored in the dark at 0°-5° C.

EXAMPLE 4

Hydrophobic Chromatography of $F_{540}$-$T_3$-Dextran Conjugate (VI)

Decyl agarose (Miles Labs, 1.0 ml packed volume) was added to the conjugate solution (6.0 ml, O.D. at 545 nm of 1.67, previously run through Sephadex G-50) in a graduated centrifuge tube. The tube was rotated slowly for 4 h in the dark at room temperature. Meanwhile, a small column (0.5×10 cm) of decyl agarose (1 ml) was prepared.

After 4 h the tube was centrifuged at 2500 rpm for 5 min. The supernatant was removed and the pellet suspended in buffer (ca. 2 ml) (0.05M phosphate, pH 8.0). The suspension was added to the top of the previously prepared column. Additional buffer (ca. 2 ml) was used to rinse out the tube; this was also added to the column. The column was eluted with a fast flow rate (20 drops per minute). After all the rinse buffer had eluted, more buffer (ca. 10 ml) was run through the column; then 0.5% Tween 20 (Sigma, ca. 15 ml) in buffer was run through the column. Fractions (ca. 2.5 ml) were taken; a peak in the UV (λ545) was observed. Each fraction was checked in the assay described below for separation (low to high calibrators) and serum interaction. Fractions which have less than 10% serum interaction and at least 85% of low-high separation of the peak fraction were pooled and used for the development of a $T_3$ assay. The supernatant, buffer wash, and trail of UV peak were not usable. Approximately 20% of the total O.D. put on decyl agarose (7.8 ml×0.25 O.D.) was isolated as good material.

The assay protocol was as follows. A sample (40 µl) is drawn up into a diluter and dispensed with 200 µl of buffer containing $T_3$ (30 mg/ml) into a croan cup. To this cup, 50 µl anti $T_3$ labeled with a fluorescence quencher (Dye/protein ratio≃20) and 50 µl $F_{540}$-$T_3$-dextran conjugate (750 nM) along with 700 µl buffer are added and the rate of quenching of fluorescence is determined over 30 seconds.

Assay buffer was 0.2M Tris containing 75 mM barbital and 0.2M NaCl adjusted to pH 8.0. The assay is performed using a low calibrator (~25% uptake response) and a high calibrator (~65% uptake response). Calibrators were prepared by blending a mixture of TBG free freon treated human serum and normal freon treated serum.

A number of different methods of purification for fluorescer-dextran-$T_3$ conjugate were compared involving a variety of column packings to determine whether there was any improvement in the separation between the low calibrator and the high calibrator.

TABLE 1

| Column Material | Result | Low-High Separation (Arbitrary Fluorescence Units) |
| --- | --- | --- |
| G-50 Sephadex | No discrimination | 156 |
| LH-20 Sephadex | No discrimination | |
| Hexyl agarose | No discrimination | |
| Hydroxyapatite | No discrimination | 140* |
| RP-2 | ** | |
| Decylagarose: | | 259 |
| Miles Sigma | | 222 |

*Best cut
**Product did not come off the column

Table 1 indicates the effect of a variety of column materials on the separation between the low and high calibrator, indicating the presence or absence of interference by serum.

It is evident from the above results that the subject method provides a substantial improvement in a reagent subject to non-specific interference from serum.

Although the foregoing invention has been described in some detail by way of illustration and example for purposes of clarity of understanding, it will be obvious that certain changes and modifications may be practiced within the scope of the appended claims.

What is claimed is:

1. In a method for determining a hydrophobic analyte employing a reagent comprising said analyte and a fluorescent label conjugated to a water soluble polysaccharide carrier, wherein said reagent is subject to nonspecific interference from serum components, the improvement which comprises, contacting said reagent with a lipid modified water insoluble polysaccharide reagent separating said reagent from said polysaccharide reagent.

2. A method according to claim 1, wherein said polysaccharide reagent is agarose.

3. A method according to claim 1, wherein said lipid modified agarose is dextran and has lipids of from about 10 to 14 carbon atoms.

4. A method according to claim 3, wherein said lipid has 10 carbon atoms.

5. A method according to claim 4, wherein said ligand is triiodothyronine.

6. A method according to claim 1, wherein said contacting and separating comprises passing said reagent through a lipid modified agarose column and eluting with a solution containing a small amount of a non-ionic detergent.

7. A method according to claim 6, wherein said detergent is Tween 20.

8. In a method for determining a polyiodothyronine employing a reagent comprising polyiodothyronine and a fluorescent label conjugated to dextran in combination with antibodies to polyiodothyronine conjugated with quencher molecules wherein said reagent is subject to non-specific interference from serum components, the improvement which comprises, treating said reagent with lipid modified dextran, wherein said lipid is of from about 10 to 14 carbon atoms.

* * * * *